United States Patent [19]

Lovegrove et al.

[11] Patent Number: 4,919,938

[45] Date of Patent: Apr. 24, 1990

[54] SUSTAINED RELEASE PHARMACEUTICAL COMPOSITIONS IN ORAL DOSAGE FORM

[75] Inventors: Claire J. Lovegrove, Ware; David A. Rawlins, Tewin; Anthony J. Phillips, Little Hadham; David A. Tainsh, Buntingford, all of England

[73] Assignee: Merck Sharp & Dohme Ltd., Hoddesdon, England

[21] Appl. No.: 418,821

[22] Filed: Oct. 4, 1989

Related U.S. Application Data

[63] Continuation of Ser. No. 68,986, Jul. 1, 1987, abandoned.

[30] Foreign Application Priority Data

Jul. 9, 1986 [GB] United Kingdom ............... 8616669

[51] Int. Cl.$^5$ ............................ A61K 9/36; A61K 9/16
[52] U.S. Cl. .................................... 424/480; 424/482; 424/473; 424/494; 424/495; 424/497
[58] Field of Search ...................... 424/480, 473, 482

[56] References Cited

U.S. PATENT DOCUMENTS

| | | | |
|---|---|---|---|
| 4,252,786 | 2/1981 | Weiss et al. | 424/480 |
| 4,420,480 | 12/1983 | Jones | 514/234 |
| 4,459,279 | 7/1984 | Stricker et al. | 424/480 |
| 4,505,890 | 3/1985 | Jain et al. | 424/21 |
| 4,572,833 | 2/1986 | Pedersen et al. | 424/480 |
| 4,610,870 | 9/1986 | Jain et al. | 424/19 |
| 4,656,167 | 4/1987 | Nozulak et al. | 514/228 |
| 4,693,896 | 9/1987 | Wheatley et al. | 424/480 |
| 4,695,591 | 9/1987 | Hanna et al. | 424/488 |
| 4,716,040 | 12/1987 | Panoz | 424/468 |

Primary Examiner—William R. Dixon, Jr.
Assistant Examiner—Jerry D. Johnson
Attorney, Agent, or Firm—William H. Nicholson; Manfred Polk; Joseph F. DiPrima

[57] ABSTRACT

Oral dosage forms for neutral, zwitterions or slats of acidic or basic drugs with approximate zero order release kinetics comprise a core matrix of the drug, and a gelling polymer, the matrix being coated with a water permeable but insoluble polymer.

3 Claims, No Drawings

SUSTAINED RELEASE PHARMACEUTICAL COMPOSITIONS IN ORAL DOSAGE FORM

This application is a continuation of application Ser. No. 07/068,986, filed July 1, 1987 abandoned.

SUMMARY OF THE INVENTION

This invention is concerned with a sustained release oral dosage form for medicaments wherein the dosage form has approximate zero-order release characteristics, whereby plasma levels of the medicament tend to remain largely constant for an appropriate time. The dosage form comprises a coated matrix of the medicament in a cellulosic gelling agent. The coating constits of a water permeable, but low solubility polymer such as a derivatized cellulose which may be the same as or different from the core polymer and which provides an initial delay before main release of medicament. The formulation of this invention may also contain a buffer to maintain the release rate of an acidic or basic drug independent of pH as the dosage form moves through the alimentary canal.

BACKGROUND OF THE INVENTION

Oral dosage forms for the sustained release of drugs from water insoluble and slowly soluble matrices are well known in the prior art such as U.S. Pat. No. 4,389,393 and the release is known to occur by a diffusion process. As the diffusion path length increases with time, a linear plot of percent released versus $t^{\frac{1}{2}}$ is obtained which is not ideal for maintenance of a plasma level which is intended to be more or less constant for an appropriate time.

Similarly, matrix systems usually exhibit an initial rapid release (but "burst" effect) of active ingredient which promotes increased plasma levels and may cause the adverse reactions which the dosage form was designed to minimize.

U.S. Pat. Nos. 4,505,890 and 4,610,870 describe controlled release formulations having a core containing gelling agent and a coat comprising either a film-forming agent and plasticizer or a hydrophilic polymer and a hydrophobic polymer. However in thos formulations, the core contains either from 8–14%, or from 5–15% of gelling agent.

With the present invention the "burst" effect has been eliminated by providing the matrix with a coating material that provides an additional barrier to diffusion of water into the matrix and drug solution out of the matrix to the external environment.

DETAILED DESCRIPTION OF THE INVENTION

The invention provides a sustained release pharmaceutical composition in oral dosage form which comprises: (1) a core matrix containing at least 20% of a derivatized cellulosic gelling agent, a medicament homogeneously dispersed therein and optionally pharmaceutically accetable excipients; and (2) a coating alyer surrounding the core matrix, the coating material being a slowly soluble, water ermeable derivatized cellulosic polymer.

The derivatized cellulosic gelling agents useful as the core matrix in the novel dosage form of this invention include: methycellulose, such as Methocel ® A4M (Dow Chemical Co.); hydroxypropylmethylcellulose, (HPMC) suh as Methocel ® E4M, F4M, or K4M (Dow Chemical Co.); or hydroxypropyl-cellulose (HPC).

The preferred polymer for use as the matrix is a hydroxypropylmethylcellulose, especially with a viscosity of about 4000 centipoises for a 2% w/v aqueous solution at 20° C., for example Methocel ® K4M.

The coating layer polymer does not contain any medicament. It may comprise any of the above described gelling agents compressed onto the core. Preferably however the coating layer is a water permeable, water insoluble film forming agent, such as ethyl cellulose or cellulose acetate phthalate; or acrylic resins such as the copolymers of acrylic and methacrylic acid esters. The preferred polymer for use as a coating material is ethylcellulose applied as a dispersion.

Examples of drugs useful in the novel formulations are (+)-trans-1a,2,3,4a,5,6-hexahydro-9-hydroxy-4-(1-propyl)-4H-naphth[1,2-b]-1,4-oxazine, enalapril, amitriptyline, cyproheptadine, cyclobenzoprine, timolol, propranolol, betaxolol, indomethacin, sulindac, diflunisal, ibuprofen, and norfloxacin.

The medicaments useful in the novel formulation of this invention may be weak bases, such as primary or secondary amines, or weak acids, such as carboxylic acids and their salts. The salts of the weak bases are preferably acid addition salts with strong acids such as hydrochloric, hydrobromic, phosphoric, sulfuric or maleic acid. The salts of the carboxylic acids are normally sodium or potassium salts. Where appropriate the active ingredient may be in zwitterionic form e.g. as an internal salt or betaine.

Medicaments which are weak acids or bases and their salts display an aqueous solubility that in most cases is dependent on the pH of the aqueous environment. Thus as the pH of the gastrointestinal tract varies from 1 to 7.5, the solubility of the medicament and consequently its release from the prior art dosage forms will vary depending upon its position in the alimentary canal and time after administration.

In a further aspect of this invention, the pH dependent release is eliminated by including a buffer in the core matrix. This produces a microenvironment of constant pH whereby the solubility of the drug is unchanged regardless of the pH of the body fluids of the external environment.

Buffering agents useful with the salts of basic drugs include, for example, citric acid, tartaric acid, succinic acid, maleic acid, and fumaric acid. A preferred buffer is citric acid.

Buffering agents useful with salts of the acidic drugs include, for example, tromethamine.

The optional pharmaceutically acceptable exceipients assist in the manufacture of the novel formulations and include conventional materials such as lactose, magnesium stearate, talc, and sorbitol.

The novel formulation conveniently weighs about 50 to 1000 mg, for example 100 to 400 mg. The core comprises about 20 to 60%, and prferably about 30 to 60% by weight of polymer, the remainder being up to 50% of medicament, for example from 0.41 to 20% w/w mg of active ingredient, and from 2.08 to 12.5% w/w of buffer plus inert excipients.

The coating may conveniently be applied either by compression or by spraying. For a compression tablet, the coating may comprise 30 to 100% of the weight of the core, preferably about 50% w/w. This may tpically represent 50–100 mg of coating material. When a film forming coating layer is employed, the coat may comprise from 2 to 6% of core weight, preferably from 3 to 5%. This may typically represent a weight of coating of from 2 to 10 mg.

In use, the coating layer of the product of this invention avoids the initial burst of release of medicament by providing an initial barrier to surface diffusion of medicament. Because the coating layer is water permeable, water and gastric fluid is able to permeate through the coating layer causing swelling of the core and dissolution of the medicament therein. During this initial period, usually approximately 1-2 hours, a small amount of mediament diffuses out at a slow rate, through the coating, hence providing the initial slow release. When a film-forming coating layer is employed, then as the gellation increases, the core expands until the coating material is ruptured. At this stage release is caused solely by diffusion from the gelled core matrix. If the coating comprises a gelling agent, the medicament diffuses into the coating layer and is subsequently released therefrom.

The formulations of the inventions are illustrated by the following Examples. In the following examples the medicament is the direct acting dopaminergic agent, (+)-trans-1a,2,3,4a,5,6-hexahydro-9-hydroxy-4-(1-propyl)-4H-naphth[1,2-b]-1,4-oxazine hydrochloride (I). Its use and the use of particular polymers, buffers, and inert additives and fillers in the particular amounts shown are not intended to limit the scope of this invention but are exemplary only. Other basic or acidic drugs and their salts, neutral or zwitterionic compounds and other polymers, buffers and inert additivies and fillers with similar properties can be used.

All matrix formulations, independent of potency were manufactured by the following general technique.

Compound I, HPMC K4M and lactose are mixed in a suitable blender. Citric acid is dissolved in a suitable volume of ethanol or water and added with mixing to the drug owders to obtain a suitable granular consistency. The mass is screened, dried, re-screened, lubricated with magnesium stearate and compressed on 10/32" (7.9 mm) punches.

EXAMPLE 1 core Formulae and Their Release Characteristics

| (a) Compound I | 1.0 mg |
| Citric Acid | 10 mg |
| HPMC K4M | 80 mg |
| Lactose | 108 mg |
| Magnesium stearate | 1 mg |
| Total | 200 mg |

| Time (hrs) | Cumulative % dose released at pH 1.2 |
|---|---|
| 2 | 46 |
| 4 | 63 |
| 6 | 81 |
| 8 | 90 |

| (b) Compound I | 5 mg |
| Citric Acid | 10 mg |
| HPMC K4M | 80 mg |
| Lactose | 104 mg |
| Magnesium stearate | 1 mg |
| Total | 200 mg |

| | Cumulative % dose released | | |
|---|---|---|---|
| Time (hrs) | pH 1.2 | pH 5.5 | pH 7.5 |
| 2 | 37 | 39 | 31 |
| 4 | 56 | 56 | 57 |
| 6 | 71 | 71 | 69 |
| 8 | 85 | 80 | 79 |
| 10 | 91 | 91 | 85 |

| (c) Compound I | 5 mg |
| Citric Acid | 5 mg |
| HPMC K4M | 80 mg |
| Lactose | 109 mg |
| Magnesium stearate | 1 mg |
| Total | 200 mg |

| | Cumulative % dose released | |
|---|---|---|
| Time (hrs) | pH 1.2 | pH 7.5 |
| 2 | 41 | 43 |
| 4 | 61 | 64 |
| 6 | 77 | 80 |
| 8 | 86 | 91 |
| 10 | 91 | 96 |

| (d) Compound I | 10 mg |
| Citric Acid | 10 mg |
| HPMC K4M | 80 mg |
| Lactose | 99 mg |
| Magnesium stearate | 1 mg |
| Total | 200 mg |

| | Cumulative % dose released |
|---|---|
| Time (hrs) | pH 1.2 |
| 2 | 45 |
| 4 | 68 |
| 6 | 80 |
| 8 | 90 |

| (e) Compound I | 24 mg |
| Citric Acid | 5 mg |
| HPMC K4M | 80 mg |
| Lactose | 90 mg |
| Magnesium stearate | 1 mg |
| Total | 200 mg |

| | Cumulative % dose released | |
|---|---|---|
| Time (hrs) | pH 1.2 | pH 7.5 |
| 2 | 38 | 45 |
| 4 | 60 | 70 |
| 6 | 77 | 82 |
| 8 | 89 | 91 |
| 10 | 95 | 96 |

(f) The Effect of Polymer Content on Release Characteristics

| | HPMC content (% w/w) | | | |
|---|---|---|---|---|
| | 20 | 30 | 40 | 60 |
| Compound I | 5 mg | 5 mg | 5 mg | 5 mg |
| HPMC K4M | 40 mg | 60 mg | 80 mg | 120 mg |
| Lactose | 144 mg | 124 mg | 104 mg | 64 mg |
| Citric Acid | 10 mg | 10 mg | 10 mg | 10 mg |
| Magnesium Stearate | 1 mg | 1 mg | 1 mg | 1 mg |
| Total | 200 mg | 200 mg | 200 mg | 200 mg |

| | Cumulative % dose released at pH 1.2 | | | |
|---|---|---|---|---|
| Time (hrs) | 20% | 30% | 40% | 60% |
| 2 | 58 | 48 | 44 | 36 |
| 4 | 82 | 74 | 66 | 54 |
| 6 | 98 | 90 | 81 | 68 |
| 8 | 100 | 98 | 91 | 80 |
| 10 | — | 100 | 97 | 87 |

(g) The Effect of Tablet Size on Release Characteristics

The composition described in Example 1.(b) above was prepared and the granulation compressed at 100, 200 and 400 mg on 7/32" (5.6 mm), 10/32" (7.9 mm) and 13/32" (10.3 mm) punches respectively.

| | Cumulative % dose released at pH 1.2 | | |
|---|---|---|---|
| Time (hrs) | 7/32" | 10/32" | 13/32" |
| 2 | 48 | 40 | 37 |

-continued

| Time (hrs) | Cumulative % dose released at pH 1.2 | | |
|---|---|---|---|
| | 7/32″ | 10/32″ | 13/32″ |
| 4 | 74 | 60 | 56 |
| 6 | 87 | 79 | 71 |
| 8 | 91 | 89 | 82 |
| 10 | 94 | 95 | 90 |

EXAMPLE 2

Coating Formulae Applied to Cores

| (a) Core | | |
|---|---|---|
| Compound I | | 5 mg |
| Citric Acid | | 5 mg |
| HPMC K4M | | 40 mg |
| Lactose | | 49.5 mg |
| Magnesium stearate | | 0.5 mg |
| | Total | 100 mg |
| Coat | | |
| HPMC K4M | | 80 mg |

The granule was prepared as described earlier and compressed on ¼″ (6.4 mm) normal concave punches. The HPMC K4M coat was applied by compression using 5/16″ (7.9 mm) normal concave punches.

| Time (hrs) | Cumulative % dose released at pH 1.2 |
|---|---|
| 2 | 2 |
| 4 | 12 |
| 6 | 32 |
| 8 | 53 |
| 10 | 71 |
| 12 | 84 |

Release rate approximated to zero-order from 2-12 hours of the profile.

| (b) Core | As in Example 4.(a) | |
|---|---|---|
| Coat | HPMC K4M | 60 mg |
| Time (hrs) | Cumulative % dose released at pH 1.2 | |
| 2 | 12 | |
| 4 | 35 | |
| 6 | 58 | |
| 8 | 77 | |
| 10 | 88 | |
| 12 | 93 | |

Release rate approximated to zero-order over the first hours of the profile.

| (c) Core | |
|---|---|
| Compound I | 5 mg |
| Citric Acid | 10 mg |
| HPMC K4M | 80 mg |
| Lactose | 104 mg |
| Magnesium stearate | 1 mg |
| Total | 200 mg |

The granule was prepared as described earlier and compressed on 5/16″ (7.9 mm) concave punches.

| Coating | |
|---|---|
| Aquacoat* | 372 g |
| Dibutyl sebacate | 28 g |

*An aqueous dispersion of ethylcellulose containing 30% solids.

The suspension was prepared using conventional mixing equipment and applied to the tablets using the air-suspension method. A coat weight of 8 mg per tablet was applied.

| Time (hrs) | Cumulative % dose released at pH 1.2 |
|---|---|
| 2 | 13 |
| 4 | 33 |
| 6 | 51 |
| 8 | 67 |
| 10 | 83 |
| 12 | 87 |

Release rate approximated to zero-order over the first 10 hours of the profile.

| (d) Core | As in Example 4.(c) above. | |
|---|---|---|
| Coating | Aquacoat | 77 g |
| | Myvacet 9-40 | 7 g |
| | Water | 78 g |

Myvacet 9-40 is a distilled acetylated monoglyceride plasticiser available from Eastman Chemical Products of Tennessee, U.S.A.

The coating procedure was as described above. A theoretical coat weight of 4 mg per tablet was applied.

| Time (hrs) | Cumulative % dose released | | |
|---|---|---|---|
| | pH 1.2 | pH 5.5 | pH 7.5 |
| 2 | 25 | 26 | 39 |
| 4 | 41 | 49 | 62 |
| 6 | 62 | 67 | 76 |
| 8 | 77 | 81 | 85 |
| 10 | 87 | 92 | 90 |
| 12 | 93 | 100 | 92 |

The pH dependence has little in vivo significance and is a function of the pH solubility profile of the coat. Under in vivo conditions release will initiate shortly after ingestion at about pH 1 and the "burst effect" will consequently be eliminated. A pH of 7-7.5 will not be achieved until 4 to 5 hours after dosing and if the rates are examined after this period they are seen to be essentially independent of pH.

(e) The Effect of Matrix Polymer Content on Release Characteristics of Coated Tablets Core Formulae: As in Example 1(f) above
Coating: As in Example 2(d) above The coating procedure was as described above. A therotical coat weight of 5.5 mg per tablet was applied.

| Time/Hrs | Cumulative % dose released at pH 1.2 HPMC Content (% w/w) | | |
|---|---|---|---|
| | 30% | 40% | 60% |
| 2 | 12.3 | 25.4 | 26.6 |
| 4 | — | 40.9 | — |
| 6 | — | 62.2 | — |
| 8 | — | 77.2 | — |

-continued

| | Cumulative % dose released at pH 1.2 HPMC Content (% w/w) | | |
|---|---|---|---|
| Time/Hrs | 30% | 40% | 60% |
| 10 | 83.7 | 86.5 | 81.0 |
| 12 | 92.1 | 92.7 | 88.6 |

Flexibility in modifying the release profile can be achieved by altering the polymer contents of the tablet core and coat.

What is claimed is:

1. A sustained release pharmaceutical composition in tablet form consisting essentially of:
   (1) a core matrix containing 20% to 60% w/w of a hydroxypropylmethylcellulose gelling agent, the remainder of the core matrix containing 0.41% to 20% w/w of (+)-trans-1a,2,3,4a,5,6-hexahydro-9-hydroxy-4-(1-propyl)-4H-naphth[1,2-b]-1,4-oxazine hydrochloride and 2.08 to 12.5% w/w of buffering agent homogeneously dispersed therein, plus suitable pharmaceutically acceptable excipients; and
   (2) A coating layer surrounding the core matrix, the coating being a slowly soluble, water permeable ethyl cellulose polymer.

2. The oral dosage form of claim 1, wherein the buffering agent is citric acid.

3. The oral dosage form of claim 2 wherein a 2% w/w aqueous solution of the hydroxypropylmethylcellulose at 20° C. has a viscosity of about 4000 centipoises.

* * * * *